(12) United States Patent
Schrörs

(10) Patent No.: US 9,132,218 B2
(45) Date of Patent: Sep. 15, 2015

(54) MEDICAL BLOOD-TREATING APPARATUS FOR THE EXTRA-CORPOREAL TREATMENT OF BLOOD

(75) Inventor: Alexander Schrörs, Frankfurt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1025 days.

(21) Appl. No.: 12/665,423

(22) PCT Filed: Jun. 14, 2008

(86) PCT No.: PCT/EP2008/004805
§ 371 (c)(1),
(2), (4) Date: Feb. 9, 2010

(87) PCT Pub. No.: WO2008/155077
PCT Pub. Date: Dec. 24, 2008

(65) Prior Publication Data
US 2011/0022103 A1    Jan. 27, 2011

(30) Foreign Application Priority Data
Jun. 19, 2007    (DE) .......................... 10 2007 028 133

(51) Int. Cl.
*A61N 1/00*    (2006.01)
*A61M 1/16*    (2006.01)
(Continued)

(52) U.S. Cl.
CPC . *A61M 1/16* (2013.01); *A61M 1/34* (2013.01); *A61M 1/36* (2013.01); *A61N 1/36003* (2013.01); *A61N 1/36017* (2013.01); *A61H 39/002* (2013.01); *A61M 2205/054* (2013.01)

(58) Field of Classification Search
CPC ............ A61N 1/36003; A61N 1/3605; A61N 1/36017; A43B 3/0005; A61B 5/04085
USPC .............. 607/2, 3, 48, 62, 144; 600/386, 388; 604/28–30
See application file for complete search history.

(56) References Cited

U.S. PATENT DOCUMENTS 4,008,712 A * 2/1977 Nyboer .......................... 600/547
4,148,321 A    4/1979 Wyss et al.
(Continued)

FOREIGN PATENT DOCUMENTS

DE    3151180    8/1982
EP    1205144    5/2002
(Continued)

OTHER PUBLICATIONS

PCT International Search Report and Written Opinion for PCT/EP08/004805, mailed on Oct. 2, 2008.

*Primary Examiner* — Christopher D Koharski
*Assistant Examiner* — Roland Dinga
(74) *Attorney, Agent, or Firm* — Kenyon & Kenyon LLP

(57) ABSTRACT

A medical blood-treating apparatus for the extra-corporeal treatment of blood has an extra-corporeal blood circuit. An arrangement for the extra-corporeal treatment of blood and an arrangement for electrical muscle stimulation (EMS) with which muscles of the patient can be stimulated in a targeted fashion during the dialysis treatment are provided. For this purpose, the arrangement for EMS has a means of generating electrical pulses, and has one or more electrodes connected to the means of generating electrical pulses. To enable targeted stimulation, the electrodes are applied to the patient's skin, e.g., the legs, during the blood treatment. Muscle stimulation during blood treatment may result in the dialysis treatment being more tolerable for the patient and increase the efficiency of the blood treatment. The blood-treating apparatus according to the invention allows an improvement in the efficiency of the blood treatment without any active sporting activity or exercise by the patient.

4 Claims, 2 Drawing Sheets

(51) Int. Cl.
*A61M 1/34* (2006.01)
*A61M 1/36* (2006.01)
*A61N 1/36* (2006.01)
*A61H 39/00* (2006.01)

(56) References Cited

U.S. PATENT DOCUMENTS

| | | | | |
|---|---|---|---|---|
| 4,790,319 | A | * | 12/1988 | Slovak .............................. 607/46 |
| 4,942,880 | A | * | 7/1990 | Slovak ........................... 600/547 |
| 2003/0032993 | A1 | | 2/2003 | Mickle |
| 2004/0064156 | A1 | | 4/2004 | Shah |
| 2005/0181016 | A1 | * | 8/2005 | Freyman et al. .............. 424/426 |
| 2006/0111754 | A1 | | 5/2006 | Rezai |
| 2007/0156200 | A1 | | 7/2007 | Kornet |
| 2008/0215247 | A1 | * | 9/2008 | Tonelli et al. .................... 702/19 |
| 2009/0138074 | A1 | * | 5/2009 | Freyman et al. .............. 623/1.38 |
| 2010/0137777 | A1 | * | 6/2010 | Kopperschmidt ........... 604/5.04 |

FOREIGN PATENT DOCUMENTS

| | | |
|---|---|---|
| JP | 57-188260 A | 11/1982 |
| WO | WO 02/23691 | 2/2002 |
| WO | WO 2007/076281 | 7/2007 |

* cited by examiner

MEDICAL BLOOD-TREATING APPARATUS FOR THE EXTRA-CORPOREAL TREATMENT OF BLOOD

FIELD OF THE INVENTION

The present invention relates to a medical blood-treating apparatus for the extra-corporeal treatment of blood having an extra-corporeal blood circuit. The present invention also relates to an arrangement for the extra-corporeal treatment of blood for use with an arrangement for electrical muscle stimulation, and to an arrangement for electrical muscle stimulation for use with an arrangement for the extra-corporeal treatment of blood.

BACKGROUND

In the event of chronic kidney failure, various methods for the extra-corporeal treatment or cleansing of the blood are used to remove substances which are normally eliminated in the urine and for the purpose of therapeutic dehydration. In haemodialysis, the patient's blood is cleansed outside the body in a dialyzer. The dialyzer has a blood chamber and a dialysis-fluid chamber, which chambers are separated by a semi-permeable membrane. During the treatment, the patient's blood flows through the blood chamber, with dialysis fluid flowing through the dialysis-fluid chamber of the dialyzer to cleanse the blood of substances which are normally eliminated in the urine.

Whereas in hemodialysis (HD), the transport of the substances of lower molecular weight through the membrane of the dialyzer is determined in essence by the differences in concentration between the dialysis fluid and the blood (diffusion), in hemofiltration (HF), substances dissolved in the plasma, and particularly substances of higher molecular weight, are removed effectively by a high flow of liquid through the membrane of the dialyzer (convection). In hemofiltration the dialyser acts as a filter. A combination of the two methods is called hemodiafiltration (HDF).

In the extra-corporeal treatment of blood, such as hemodialysis for example, the following problems arise. During the dialysis, it is essentially only the patients' blood which is cleansed but not the cellular and intra-cellular compartments. Because the transport of the toxins dissolved in water into the blood takes place only very slowly, better results are obtained from a dialysis treatment extending over quite a long period of time than from a short dialysis. Because of the effective cleansing of the blood and the poor cleansing of the cellular and intra-cellular compartments, high concentration gradients arise. What therefore occurs immediately after the dialysis is a balancing of the concentrations of the toxins between the compartments and the blood, an occurrence which is referred to as a rebound. The rebound places a considerable stress on the patient's circulation. In certain cases, the rebound may even result in circulatory failure after dialysis. A further problem arises from the fact that the dialysis treatment has to be carried out in a sitting or lying position, because the patient's radius of action is restricted by the dialysis machine. Physical immobility however causes an inhibition of blood flow to the peripheral parts of the body, and particularly the legs, for which reason the blood is less well cleansed in these parts.

In the specialized field of dialysis, it is widely known that regular sporting activity by the patient has a beneficial effect on the dialysis treatment (Nephron 42: 311-316 (1986) Exercise Training Reduces Coronary Risk and Effectively Rehabilitates Hemodialysis Patients, Andrew P. Goldberg et al.).

It is also known that the efficiency of dialysis treatment can be significantly increased if the patient indulges in active physical activity during the dialysis treatment. The so-called rebound effects can also be reduced in this way. It is known that physical activity by the patient during the dialysis treatment results in improved blood circulation in the body, which means that the flow of blood is better through areas in which it is only weak, by which means the cleansing of the blood is improved. What is seen with physical activity during the dialysis is not only a slight rise in pulse rate and blood pressure but also improved metabolic exchange between the compartments and an increase in clearance, which is equivalent to dialysis treatment of longer duration. What is also seen is a reduction in the rebound of urea, creatinine and potassium (Nephron 43: 87-92 (1986), Effects of Exercise Training during Hemodialyses, Patricia L. Painter et al.; Nephrol Dial Transplant (1999) 14: 2927-2931, The effect of exercise during haemodialysis on solute removal, Chiew H. Kong et al.).

Also known as measures which stimulate the circulation and encourage blood flow are massages particularly of the patient's legs, although these are found to be labor-intensive and cost-intensive. Also, the results from massages are difficult to repeat.

The studies of the effect of sporting activity on the results of dialysis treatments were carried out on patients whose physical fitness was sufficiently good. However, because of the high average age of dialysis patients, which is approximately 67 years, the physical fitness of many such patients is no longer adequate for them to themselves actively perform sporting exercises during the dialysis treatment. Attention must also be paid to the fact that, when there are movements by the patient, the venous and/or the arterial needle may accidentally be disconnected during the dialysis. Therefore, any sporting activity by the dialysis patient during dialysis treatment requires closer monitoring, in which case the requirements which the technical safety precautions for quickly detecting the disconnection of a needle need to meet have to be made more stringent, which likewise involves higher costs.

In the field of sports medicine, it is known for the fitness of sportsmen and athletes to be increased by what is termed electrical muscle stimulation, also referred to as EMS. In this, the targeted electrical stimulation of the muscles is used not only for training but also for warming up, relaxing and accelerated regeneration. It is also known for electrical muscle stimulation (EMS) to be used for therapeutic measures.

US 2005/0131489 A1 for example describes the use of electrical muscle stimulation for preventing venous thromboses in immobile patients, such as in intensive care units, for example. An arrangement for muscle stimulation for the same application is also known from WO 03/063960 A2.

The object underlying the invention is to provide a medical blood-treating apparatus which allows blood to be treated extra-corporeally with greater efficiency. A further object of the invention is to specify a method for treating blood extra-corporeally with greater efficiency. It is also an object of the invention to provide an arrangement for the extra-corporeal treatment of blood for use with an arrangement for electrical muscle stimulation, and an arrangement for electrical muscle stimulation for use with an arrangement for the extra-corporeal treatment of blood, with which arrangements the efficiency of the extra-corporeal treatment of the blood can be increased.

SUMMARY

The medical blood-treating apparatus according to example embodiments of the present invention is characterized in that there is provided, in addition to the arrangement for the extra-corporeal treatment of blood, an arrangement for electrical muscle stimulation (EMS) with which muscles of the patient can be stimulated in a targeted fashion during the dialysis treatment. For this purpose, the arrangement for electrical muscle stimulation (EMS) has a means of generating electrical pulses, and has one or more electrodes which are connected to the means of generating electrical pulses. To enable muscles of the patient, and particularly muscles in the leg region, to be stimulated in a targeted fashion, the electrodes are applied to the patient's skin, and in particular to the patient's legs.

It has been found that muscle stimulation during blood treatment, such as, e.g., during hemodialysis treatment, results in the dialysis treatment being more tolerable for the patient and in the efficiency of the treatment being increased. The explanation for this is an improved transfer of "waste products" from the muscular tissue into the blood stream.

It is an advantage that the blood-treating apparatus according to example embodiments of the present invention allows an improvement to be made in the efficiency of the blood treatment, i.e. of the hemodialysis treatment for example, without any active sporting activity or exercise by the patient. In this way, the efficiency of the dialysis treatment can be improved even for patients who are not sufficiently fit physically. Because the improvement in the efficiency of the dialysis does not presuppose any active activity by the patient, there is also no increase in the risk of a needle being disconnected. Moreover, no additional staff is required for massages accompanying the treatment.

In a preferred embodiment of the medical blood-treating apparatus, the arrangement for the extra-corporeal treatment of blood and the arrangement for electrical muscle stimulation are not operated independently of one another, but the two arrangements communicate with one another during the treatment of the blood.

The arrangement for the extra-corporeal treatment of blood preferably has an input unit for the input of parameters relevant to the blood treatment, which include both the parameters specific to the patient, such for example as the patient's age and sex, blood pressure, hematocrit and the like, and also the operating parameters of the arrangement for the extra-corporeal treatment of blood which are relevant to the blood treatment, such as, e.g., the blood flow rate and dialysis-fluid rate or the ultrafiltration rate, etc.

The arrangement for the extra-corporeal treatment of blood also preferably has a control unit for controlling components for performing the blood treatment and/or for monitoring the parameters relevant to the blood treatment. These components include, for example, the blood pump for pumping the blood in the extra-corporeal blood circuit at the preset blood-flow rate or the dialysis-fluid pump for pumping the dialysis fluid at the preset dialysis-fluid rate. The parameters to be monitored during the blood treatment include, for example, the blood-flow rate and dialysis-fluid rate or the ultrafiltration rate.

The arrangement for electrical muscle stimulation preferably has a control unit for controlling the means of generating electrical pulses. This control unit is preferably so designed that the shape and/or current intensity and/or amplitude and/or frequency and/or length and/or modulation time of the pulses can be set.

The control unit for controlling the components for performing and/or monitoring the blood treatment preferably co-operates with the control unit for controlling the means of generating electrical pulses in such a way that the generation of the electrical pulses can be controlled as a function of the parameters relevant to the blood treatment. In this way, it is possible for the arrangement for electrical muscle stimulation to be controlled and/or regulated as a function of the parameters relevant to the blood treatment for the purpose of achieving an optimum result from the treatment. It is, however, also possible for the arrangement for the extra-corporeal treatment of blood to be controlled and/or regulated as a function of the preset values for the generation of the electrical pulses, such as, e.g., the current intensity, amplitude, frequency, length, etc. of the pulses, which are preset by the control unit of the means of generating electrical pulses.

In an embodiment of the medical blood-treating apparatus, provision is made for the arrangement for the extra-corporeal treatment of blood and the arrangement for electrical muscle stimulation to take the form of one unit piece of equipment. The two arrangements may, for example, have a common control unit (microprocessor). It is, however, also possible for the arrangement for the extra-corporeal treatment of blood and the arrangement for electrical muscle stimulation to take the form of two separate unit pieces of equipment which are able to communicate with one another. For this purpose, the arrangement for the extra-corporeal treatment of blood and the arrangement for electrical muscle stimulation preferably each have a unit for exchanging parameters relevant to the blood treatment, which units are connected together for the transmission of these parameters. The units for exchanging the parameters relevant to the blood treatment may take the form of units for the unidirectional transmission of data from the arrangement for the extra-corporeal treatment of blood to the arrangement for electrical muscle stimulation or from the arrangement for electrical muscle stimulation to the arrangement for the extra-corporeal treatment of blood. However, bi-directional data transmission between the two arrangements is also possible, which will enable both the arrangement for electrical muscle stimulation to be controlled and/or regulated as a function of the state of operation of the arrangement for the extra-corporeal treatment of blood, and the arrangement for the extra-corporeal treatment of blood to be controlled and/or regulated as a function of the state of operation of the arrangement for electrical muscle stimulation.

In a preferred embodiment, the exchange of the parameters relevant to the blood treatment between the two arrangements takes place via a wired connection. For this purpose the two arrangements, which may have conventional interfaces, are connected together by means of a conventional connecting cable.

An alternative embodiment makes provision for a non-wired connection, and in particular a radio connection, between the two arrangements. The transmission of data other than by wire is also possible with an optical connection.

Another particularly preferred embodiment makes provision for the electrodes of the arrangement for electrical muscle stimulation and/or the connections for the electrodes to be incorporated in a means of enabling the patient to lie and/or sit down. As a result the electrodes are always ready for connection to the patient and it is particularly easy for the electrodes to be connected to the patient.

The method according to the invention for the extra-corporeal treatment of blood may be characterized in that, during the extra-corporeal treatment of blood in which, in an extra-corporeal blood circuit, a patient's blood flows to a blood-treating unit and blood from the blood-treating unit flows back to the patient, muscles of the patient are stimulated in a targeted fashion by means of electrical pulses as an accompaniment to the treatment.

Example embodiments of the present invention are explained in detail below by reference to the drawings.

DETAILED DESCRIPTION

The medical blood-treating apparatus has an arrangement A for the extra-corporeal treatment of blood and an arrangement B for electrical muscle stimulation (EMS).

Figure 1:
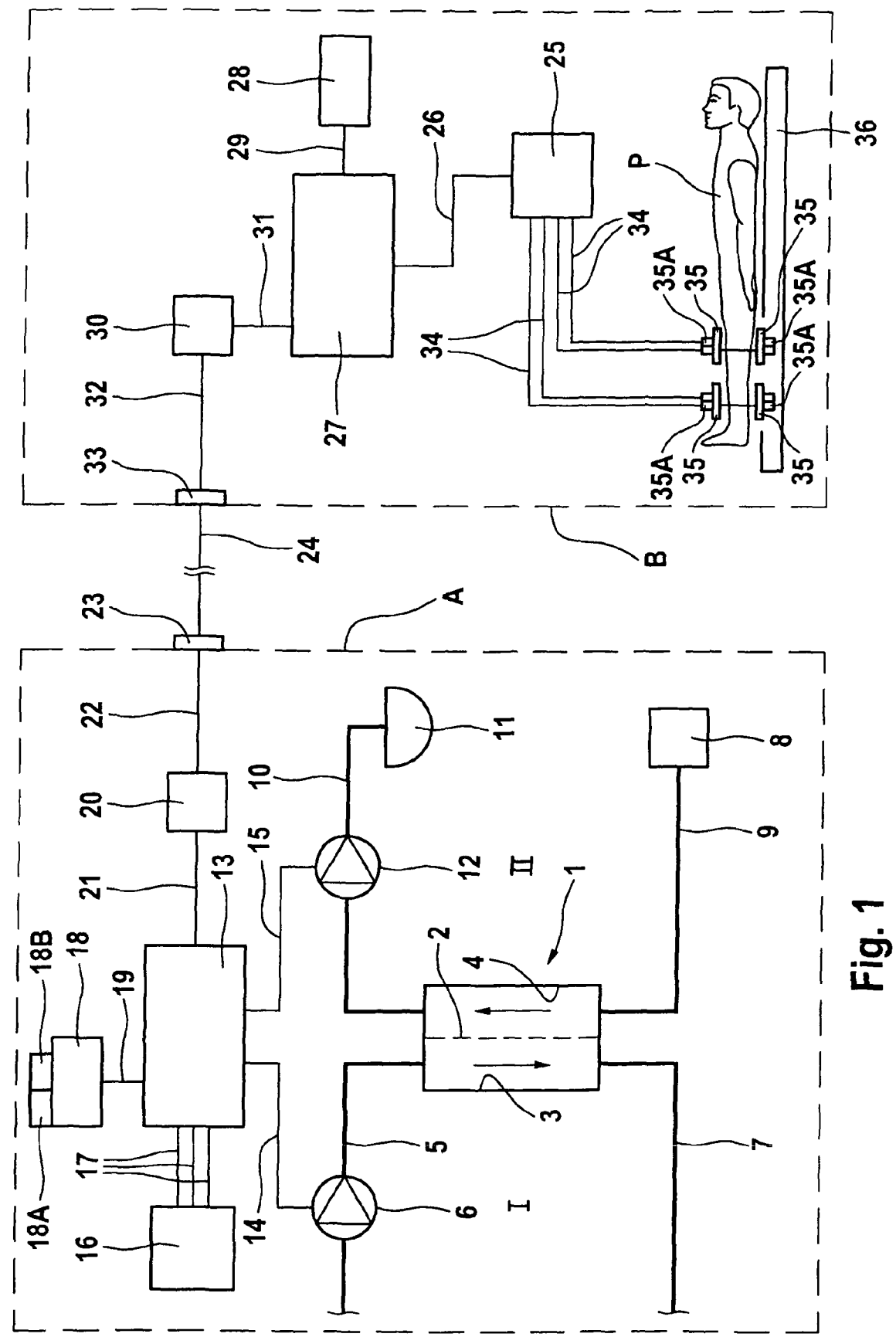
FIG. 1 is a highly simplified schematic view showing an example embodiment of medical blood-treating apparatus according to the present invention having an arrangement for the extra-corporeal treatment of blood and an arrangement for electrical muscle stimulation.

In the embodiment shown in FIG. 1, the arrangement for the extra-corporeal treatment of blood and the arrangement for electrical muscle stimulation take the form of two separate unit pieces of equipment A, B which are able to communicate with one another. The arrangement A for the extra-corporeal treatment of blood is a hemodialysis arrangement in the present embodiment. The dialysis arrangement has a dialyzer 1 which is divided into a blood chamber 3 and a dialysis-fluid chamber 4 by a semi-permeable membrane 2. Connected to the inlet to the blood chamber 3 is an arterial blood line 5 into which a blood pump 6 is connected. Running from the outlet of the blood chamber 3 is a venous blood line 7. The arterial and venous needles for connecting the dialysis arrangement to the patient have not been shown for greater clarity.

Fresh dialysis fluid is made available in a dialysis-fluid source 8. From the dialysis-fluid source 8, a dialysis-fluid infeed line 9 runs to the inlet of the dialysis-fluid chamber 4 of the dialyzer 1, while a dialysis-fluid takeaway line 10 runs from the outlet of the dialysis-fluid chamber to a discharge outlet 11. A dialysis-fluid pump 12 is connected into the dialysis-fluid takeaway line 10.

During the hemodialysis, the patient's blood flows, in the extra-corporeal blood circuit I, through the blood chamber 3 of the dialyser 1, while dialysis fluid flows, in the dialysis-fluid system II, through the dialysis-fluid chamber 4 of the dialyser 1.

The dialysis arrangement A has a control unit 13 which is connected to the blood pump 6 and the dialysis-fluid pump 12 via control lines 14, 15. The control unit 13 presets the speed of revolution of the blood and dialysis-fluid pumps 6, 12 in such a way that a given blood flow and dialysis-fluid flow are set. As well as the blood and dialysis-fluid pumps, the dialysis arrangement also has other components for performing the blood treatment but these, once again, have not been shown for greater clarity. They include, for example, a balancing device, shut-off members, etc. These components also are actuated by the control unit 13 to enable the dialysis treatment to be performed. A regulating unit may also be provided in place of the control unit 13 for the dialysis arrangement A or the piece of equipment may take the form of a unit for controlling and/or regulating. With the regulating unit, regulating loops may also be set up. Some parameters may be controlled and others may also be regulated, thus making combined control and/or regulation possible.

The control unit 13 not only controls the components required for the blood treatment but also monitors the parameters relevant to the dialysis treatment. The parameters relevant to the blood treatment are sensed by various sensors 16 which are only shown schematically and which are connected to the control unit 13 via data lines 17.

The dialysis arrangement also has an input unit 18 which can be used for the input of the parameters relevant to the blood treatment. The parameters may for example be input manually on a keyboard 18A or may be read in from a memory card 18B (patient card). The input unit 18 is once again connected to the control unit 13, by a data line 19.

To communicate with the arrangement B for electrical muscle stimulation (EMS), the dialysis arrangement A has a unit 20 for the transmission, preferably bi-directional, of the parameters relevant to the blood treatment, which unit 20 is connected to the control unit 13 via a data line 21. The unit 20 may be a conventional interface which is connected via a data line 22 to a plug 23 to which a data cable 24 may be connected. It is however also possible for the unit 20 to have a transceiver for transmitting the data in the form of radio signals or optical signals. When this is the case, the line 22 and the plug 23 are dispensed with.

The arrangement B for electrical muscle stimulation has a means 25 of generating electrical pulses, which pulses serve to stimulate the patient's muscles during the blood treatment. The means 25 of generating the electrical pulses is connected to a control unit 27 via a control line 26. The control unit 27 controls the means 25 in such a way that the electrical pulses are of a given shape, current intensity, amplitude, frequency and length. The modulation time of the pulses can also be set. The pulse shape is characteristic of the way in which an individual pulse varies over time. Square-wave pulses, for example, are generated. The current intensity should always be set to be such that an adequate muscular contraction takes place but the muscle stimulation should always be (well) below the pain threshold. What is meant by amplitude is the maximum current intensity of an individual pulse. The pulse width gives the duration of an individual pulse over time and it too, as well as the amplitude, determines the strength of the muscular contraction. What is meant by frequency is the number of individual pulses per second. Frequencies in a range from approx. 2 to 90 hertz are preferably set. As well as this, the modulation times may also be set, these specifying the variation in the amplitude of the individual pulses over time.

The above-mentioned variables may be input manually with an input unit 28, such for example as a keyboard, which is connected to the control unit 27 via a data line 29.

In place of the control unit 27 for the arrangement B for electrical muscle stimulation, a regulating unit may also be provided or the piece of equipment may take the form of a unit for control and/or regulation. With the regulating unit, regulating loops may also be set up. Some parameters may be controlled and others may also be regulated, thus making possible combined control and/or regulation.

The arrangement B for electrical muscle stimulation has a unit 30 for transmitting the data intended for the treatment to the dialysis arrangement A or for receiving data from the dialysis arrangement. In the present embodiment, the unit 30, which is connected to the control unit 27 via a data line 31, is once again a conventional interface for the bi-directional transmission of data, to which a plug 33 is connected via a data line 32. The data cable 24 may be connected to the plug 33, thus enabling the dialysis arrangement A and the arrangement B for electrical muscle stimulation to communicate with one another. Instead of wired transmission by wire, it is also possible for data to be transmitted other than by wire. For this eventuality, the unit 30 has a transceiver which is able to transmit radio signals or optical signals. The data line 32 and the plug 33 are dispensed with in this way.

Connected to the means 25 of generating electrical pulses via lines 34 are a plurality of electrodes 35 which can be applied to the skin of the patient P and in particular to the patient's legs.

During the blood treatment, the patient P sits or lies down. The means for enabling sitting and/or lying during the treatment, i.e. the chair or bed 36 on which the patient sits and/or lies, is only shown schematically. Provided on the chair or bed 36 are connections 35A to which the electrodes 35 which are applied to the patient's skin are connected, via short connecting cables (not shown in FIG. 1) if required. The connections 35A for the electrodes 35, such as plugs or sockets for example, are connected to the lines 34. The connections 35A for the electrodes 35 are preferably permanently incorporated in the surface for sitting or lying. Basically, it is, however, also possible for the electrodes themselves to be incorporated in the surface for sitting or lying. However, care must then be taken to ensure safe and certain contact of the electrodes with the patient's skin.

The control unit 13 of the blood treatment arrangement A and the control unit 27 of the arrangement B for electrical muscle stimulation are so designed that the shape and/or current intensity and/or amplitude and/or frequency and/or length and/or modulation time of the pulses are set as a function of the parameters relevant to the blood treatment which can be input with the input unit 18 and/or which are sensed during the blood treatment by the sensors 16. For example, electrical pulses of a different shape, current intensity, amplitude, frequency, length or modulation time may be generated at the beginning of the treatment from those at the end of the treatment. It is also possible for electrical pulses of a given shape, intensity, amplitude, etc. to be generated as a function of the parameters specific to the patient, which can be read in from the patient card or input manually. The electrical muscle stimulation may, for example, be run in such a way that the treatment time is minimized. Because the individual parameters are monitored during the blood treatment, the effects the electrical muscle stimulation has on the blood treatment can also be established. A preferred embodiment makes provision for, e.g., the control unit 13 of the dialysis arrangement A to set the parameters relevant to the blood treatment, such as treatment time, dialysis-fluid rate, etc., as a function of the nature of the electrical pulses (shape, current intensity, amplitude, etc.) and the effects of the electrical muscle stimulation, to give treatment which is optimum. The control unit 13 may also be capable of learning in this case.

Figure 2:
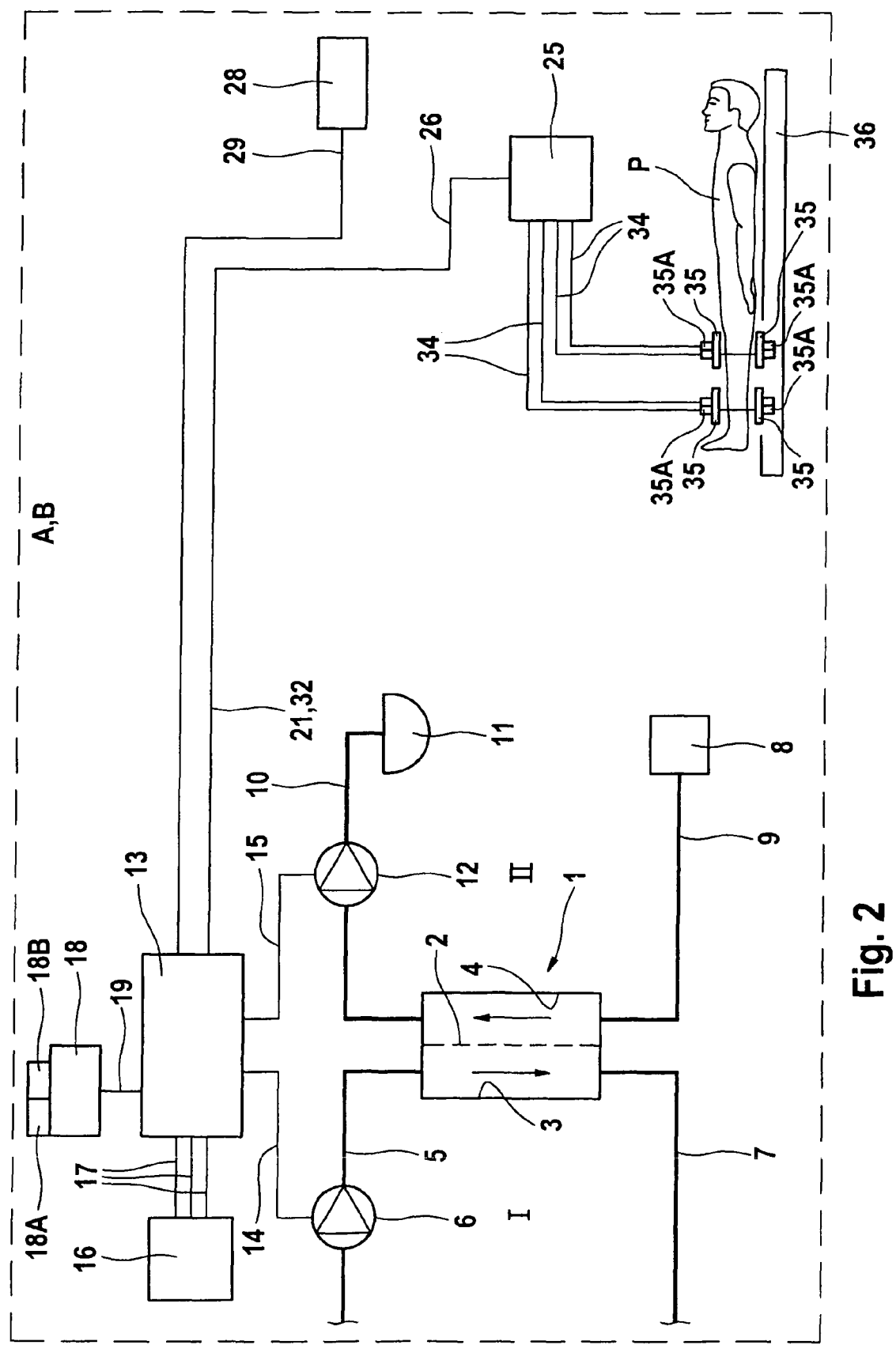
FIG. 2 is a highly simplified schematic view showing a second example embodiment of medical blood-treating apparatus according to the present invention.

FIG. 2 shows an alternative embodiment of medical blood-treating apparatus, which differs from the treating apparatus shown in FIG. 1 in that the extra-corporeal dialysis arrangement A and the arrangement B for electrical muscle stimulation are not in the form of two separate unit pieces of equipment but form one unit piece of equipment. Parts which correspond to one another are identified by the same reference numerals.

In the alternative embodiment, the extra-corporeal blood-treating arrangement A and the arrangement B for electrical muscle stimulation make use of the same control and/or regulating unit 13, to which the input unit 28 of the arrangement B for electrical muscle stimulation is also connected via the line 29. This control and regulating unit 13 is preferably the control unit (microprocessor) which is already provided in known blood-treating arrangements. Because separate control and regulating units are not provided, the interfaces can also be dispensed with in this embodiment. It is also possible for the input units 18 and 28 to be combined into one common input unit.

The invention claimed is:

1. A method for extra-corporeal treatment of blood, in which treatment a patient's blood flows, in an extra-corporeal blood circuit, to a blood-treating unit, and blood from the blood-treating unit flows back to the patient, the method comprising:

stimulating muscles of the patient with electrical pulses during the extra-corporeal blood treatment to improve the efficiency of the blood treatment; and at least one of:

setting at least one of a) a shape, b) a current intensity, c) an amplitude, d) a frequency, e) a length, or f) a modulation time of the pulses as a function of parameters relevant to the blood treatment, and at least one of controlling or regulating the stimulation as a function of a state of operation of the blood treatment or, setting at least one of a) a shape, b) a current intensity, c) an amplitude, d) a frequency, e) a length, or f) a modulation time of the pulses, and at least one of controlling or regulating the blood treatment as a function of a state of operation of the stimulation, wherein at least one of the controlling or regulating the stimulation or controlling or regulating the blood treatment is based on an improvement of the efficiency of the blood treatment.

2. The method of claim 1, wherein the blood-treating unit is at least one of a dialyzer or a filter.

3. The method of claim 1, wherein the parameters relevant to the blood treatment are preset for the blood treatment by inputting on an input unit.

4. The method of claim 1, further comprising:

monitoring the blood treatment, and sensing the parameters relevant to the blood treatment by sensors of the blood-treating unit.

* * * * *